Sept. 16, 1952 E. S. BOERNER Plant Pat. 1,129
CHRYSANTHEMUM PLANT
Filed Sept. 28, 1951
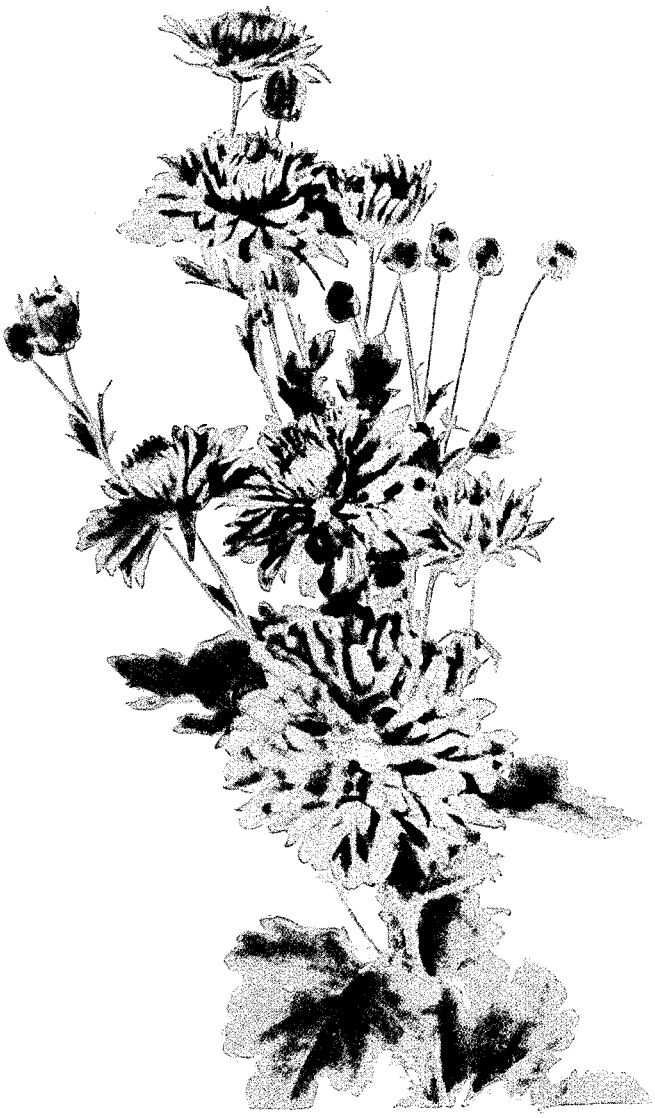
Inventor
E. S. Boerner
By Robert Cobb
Attorneys Patented Sept. 16, 1952

Plant Pat. 1,129

UNITED STATES PATENT OFFICE 1,129

CHRYSANTHEMUM PLANT

Eugene S. Boerner, Newark, N. Y., assignor to Jackson & Perkins Company, Newark, N. Y., a corporation of New York Application September 28, 1951, Serial No. 248,791

1 Claim. (Cl. 47—60)

The present invention relates to a new and distinct variety of chrysanthemum plant, originated by me by crossing the variety "Fred F. Rockwell" (Plant Patent No. 718) ×"Indiana" (unpatented).

The primary objective of this cross was to produce an earlier-blooming and brighter-colored chrysanthemum in the red shades. Accordingly, the parent "Fred F. Rockwell" was chosen for its brilliant reddish orange color, although the flowers of this variety are small, and this variety was crossed by "Indiana" which normally blooms late, but bears large, deep-red flowers. My objective was fully achieved as the result of this cross, as evidenced by the following dominant characteristics which distinguish the new variety from its parents, as well as from all other varieties of its class:

(1) Early-blooming habit (usually commencing early in September);

(2) Large size and Oxblood Red color of the blooms;

(3) Regular, semi-decorative form of the blooms; and (4) Frost-resistance of the blooms.

Asexual reproduction of this new variety by top cuttings and by underground runners at Newark, New York, shows that the foregoing characteristics come true to form and are established and transmitted through succeeding propagations.

The accompanying drawing shows specimens of the new variety, with the flowers and foliage in different stages of development.

The following is a detailed description of the new variety, as observed in the fields at Newark, New York, in the early afternoon late in the month of September, with color terminology in accordance with Ridgway's Color Standards and Nomenclature:

Parentage: "Fred F. Rockwell"×"Indiana."
Classification: Semi-decorative type.
Growth: Firm; clean; upright, tall growth; attaining a height of 30 inches.
Cold resistance: Plant winter hardy in northern New York; flowers show no frost burn with early frosts.

Blooming period: In Newark, New York, climatic area, the average date of start of blooms is September 12th and continues until heavy freeze in October and November.

Bud:
- *Color.*—When sepals first divide—Victoria Lake, Plate 1. When petals begin to unfurl—Oxblood Red, Plate 1. When half blown—inside of petals: Oxblood Red, Plate 1, overcast with Carmine, Plate 1; reverse of petals: Carmine, Plate 1.
- *Peduncle.*—Color—Cress Green, Plate 31. Strength—Slender; erect.

Bloom:
- *Size.*—3½ to 4 inches.
- *Stem.*—Strong and normal.
- *Form.*—Semi-decorative type.
- *Petalage.*—Double.
- *Color.*—Center of flower—Carmine, Plate 1, overcast with Nopal Red, Plate 1. Outer petals—Carmine, Plate 1. Base of petals—Picric Yellow, Plate 1. Inside of petals—Carmine, Plate 1. Reverse of petals—Carmine, Plate 1.
- *Petals.*—Texture—stiff. Form—oval, with very slight waving at the end.
- *Fragrance.*—Characteristic chrysanthemum.

Plant:
- *Form.*—Upright and compact.
- *Growth.*—Free.

Foliage:
- *Size.*—Large.
- *Quantity.*—Normal.
- *Color.*—Upper side—Cress Green, Plate 31; reverse side—Light Cress Green, Plate 31.
- *Texture.*—Leathery.

I claim:

A new and distinct variety of chrysanthemum plant, substantially as herein shown and described, characterized as to novelty by its early-blooming habit, by the relatively large size and Oxblood Red color of its semi-decorative type blooms, and by the frost-resistance of its blooms.

EUGENE S. BOERNER.

No references cited.